Figure 1:
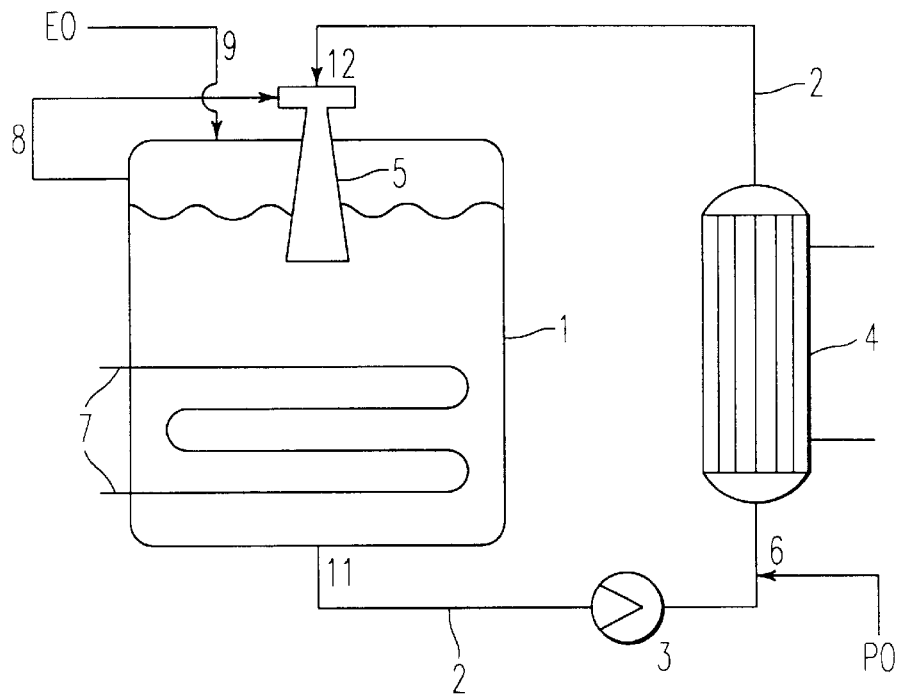

United States Patent [19]
Ellis

[11] Patent Number: 5,811,595
[45] Date of Patent: Sep. 22, 1998

[54] PROCESS FOR PREPARING ALKYLENE OXIDE REACTION PRODUCTS

[76] Inventor: Vincent Simon Ellis, Schutterslaan 11, B-3078 Everberg, Belgium

[21] Appl. No.: 499,953

[22] Filed: Jul. 10, 1995

[51] Int. Cl.$^6$ .................................................. C07C 43/11
[52] U.S. Cl. ............................................ 568/620
[58] Field of Search ............................. 568/620

[56] References Cited

U.S. PATENT DOCUMENTS

| | | | |
|---|---|---|---|
| 2,586,767 | 2/1952 | Wilson | 568/620 |
| 3,117,998 | 1/1964 | Cosby | 260/584 |
| 4,089,365 | 5/1978 | Miserlis et al. | |

FOREIGN PATENT DOCUMENTS

| | | |
|---|---|---|
| 159 262 | 3/1983 | Germany . |

*Primary Examiner*—C. Warren Ivy
*Assistant Examiner*—Jean F. Vollano
*Attorney, Agent, or Firm*—Oblon, Spivak, McClelland, Maier & Neustadt, P.C.

[57] ABSTRACT

The present invention concerns a process for preparing a highly pure adduct of one or more alkylene oxide(s) to a compound which is sufficiently reactive for an addition reaction, said process being carried out in a reaction system designed as a loop-type reactor and comprising the steps of (a) feeding a compound sufficiently reactive for the addition reaction to the reaction system and circulating said compound in the whole system; (b) deaerating the whole reaction system and injecting an inert gas; (c) adding said alkylene oxide(s) with mixing, said addition step taking place at a point of the reaction system which is upstream a heat exchanger which is assembled in the loop and serves as a means for heating; (d) quickly heating a partial amount of the reaction mixture containing freshly admixed alkylene oxide(s) to a temperature allowing a substantial degree of conversion of the reactants; (e) immediately cooling, after reaching said substantial degree of conversion of said reactants, said partial amount of said reaction mixture to a holding temperature allowing substantially no side reaction; (f) holding said reaction mixture having reached said desired degree of conversion of said reactants, in said loop-type reactor at said holding temperature allowing substantially no side reaction; and (g) freshly admixing said alkylene oxide (s) in accordance with step (c) for another reaction cycle; as well as a loop-type reactor for carrying out said process.

28 Claims, 1 Drawing Sheet

PROCESS FOR PREPARING ALKYLENE OXIDE REACTION PRODUCTS

The invention relates to a process for preparing alkylene oxide reaction products. In particular, the invention relates to a process by which addition products of alkylene oxides can be attached to compounds sufficiently reactive for the addition reaction in targeted fashion as a function of the reactivity of the reactants under reaction conditions, which ensure a reaction rate sufficiently high for practice, but, on the other hand, largely suppress the occurrence of undesired side reactions. The invention relates also to a reactor for implementing the process.

Addition products of alkylene oxides to compounds which are sufficiently reactive for the addition reaction are produced in large amounts by a large number of differently conducted processes in the chemical art. The co-reactants of the alkylene oxides are usually, but not necessarily organic compounds which are mostly liquid under the reaction conditions and which contain at least one reactive hydrogen atom bonded to an organic molecule residue via an oxygen atom, a nitrogen atom or a sulfur atom. Suited compounds include in practice monohydric or polyhydric alcohols and/ or glycols and their ethers, amines, carboxylic acids and amides, to name but a few examples. The formed reaction products are used in a plurality of fields of application, e.g. as surface-active agents (tensides), as basic cosmetic substances or in the production of polyurethanes.

In the case of a use of the products as tensides in aqueous or solvent-containing systems the distribution of homologues is i.a. of special importance for the solubility behaviour and the surface activity. The importance of this parameter is e.g. shown by the fact that, during the implementation of the addition reaction in practical chemical engineering, the reaction is controlled according to the criterion of the turbidity of the reaction mixture in a reference system.

Frequently, the quality of the products is also measured by means of the hydroxyl number. It became apparent that the molecular weight which can be determined by means of the hydroxyl number frequently does not correspond to the theoretical molecular weight calculated on the basis of the consumption of alkylene oxide, but is lower. This is attributable to the occurrence of side reactions in the alkylene oxide reactant and the reaction products, which is more or less severe as a function of the reaction temperature, the reactivity of the used alkylene oxide and the alkylene oxide concentration. Alkylene oxides do not react in the sense of the desired propagation of the chain at high concentrations and/or high reaction temperatures to increase the molecular weight, but dimerize and rearrange to less reactive by-products. Ethylene oxide dimerizes e.g. at higher temperatures and ethylene oxide concentrations to form dioxane, and propylene oxide rearranges to allyl alcohol. Moreover, water can be eliminated to form a double bond at the terminal hydroxyl function of higher molecular weight alkylene oxide addition products. Said water reacts with further alkylene oxide to polyglycols. The occurence of said side reactions can be realized from two further parameters relevant for the quality of the final products, namely an increase in the iodine number (increase in the number of the double bonds) and an increase in the content of polyglycols.

The molecular weight does practically not increase upon the occurrence of side reactions of the type mentioned above, and the distribution of homologues in the final product becomes considerably broader, i.e. inhomogeneous, and can only be controlled with difficulty in the direction to the desired uniform products. The molecular composition of the product is considerably impaired in the large group of the products the preparation of which is started with polyalcohols, in particular diols, which are to be used for the further processing to polyurethanes, and the loss of the terminal hydroxyl function with the formation of a double bond at higher temperatures leads to a less desirable product with a considerable share of monofunctional polyurethane co-reactants.

In the prior art such difficulties during the production of alkylene oxide addition products were substantially dealt with by means of a careful reaction at low temperatures and by means of an improved process conception. It was the object of all these processing improvements to increase the reaction rate by intensifying the thorough mixing of the reactants and to thus avoid a further reduction of the reaction rate upon the lowering of the temperature to avoid side reactions.

U.S. Pat. No. 2,586,767A describes a process for the production of alkylene oxide addition products, wherein in a loop-type reactor one organic compound having at least 6 carbon atoms, which contains at least one active hydrogen atom, is sprayed into a static gaseous phase containing the alkylene oxide, in which the alkylene oxide pressure is kept substantially constant, and the liquid phase is circulated with cooling and again sprayed into the static gas reaction zone until the desired molecular weight is achieved. The cooling is controlled in such fashion that a decomposition of the higher molecular weight product (in the sense of the aforementioned side reactions) is avoided. It is a disadvantage of this system that the temperature in the reaction zone must always be above the minimum reaction temperature to ensure the necessary reaction rate. Side reactions cannot be reliably prevented by this, in particular in the specific areas in which the temperature of the system greatly increases due to the exothermal reaction of the alkylene oxide with the organic compound.

The process of the PRESSINDUSTRIA company is also based on the principle revealed by U.S. Pat. No. 2,586,767 with the improvement that a special gas/liquid contactor is used for the reaction of the organic compound having a reactive hydrogen atom with the alkylene oxide. However, it also creates a stationary gas phase into which the liquid is fed. The temperature must be controlled above the minimum reaction temperature in the area of the gas/liquid contactor, as well, in order to ensure a reaction time suited for practice. Side reactions in the actual reaction areas can particularly not be avoided because a cooling can only be effected in the downstream autoclave (by means of dilution) and in the heat exchanger (by means of heat exchange) which is connected downstream of the autoclave, but not in the gas phase of the gas/liquid contactor which is insufficiently mixed and non-cooled.

A hydrogenation process is described in the article "R. F. Duveen et al.; Der Buss-Schleifenreaktor in der Öl- und Fetthartungsindustrie, in: Fette, Seifen, Anstrichmittel 84 (1st special edition 1982), 511 to 515", in which an ejector pump mixing nozzle generates large phase-exchange surfaces between reaction gas (hydrogen) and liquid (oil, fat). The supplied reaction gas is automatically constantly thoroughly mixed and recirculated together with an inert gas optionally present. If this process is applied to the reaction of organic compounds with alkylene oxides, considerable improvements as compared with the aforementioned processes result both as regards product quality and space-time yield aa well as operational reliability, which do not have any gas and liquid circulation coupled via an ejector pump mixing nozzle. A clearly improved product quality is in particular achieved due to the more exact temperature control.

A process for the safe and ecologically acceptable production of highly pure alkylene oxide adducts to organic compounds having at least one reactive hydrogen atom in a loop-type reactor with a gas and liquid circulation coupled via an ejector pump mixing nozzle is described in the European patent application 90 810 716. In said reactor, the temperature of the entire gas phase consisting of alkylene oxide and optionally inert gas in the gas circulation system of the reactor is kept below the temperature of the liquid phase during the reaction. This arrangement, as well, has the disadvantage that the temperature profile in the entire reactor is more or less uniformly high and must be above the minimum temperature necessary for a practically suitable reaction rate. A permanent cooling by means of a heat exchanger is required so that the temperature of the (intermediate) product phase does not increase beyond the value leading to the undesired formation of by-products.

The present invention was based on the object of making available an economic process for the production of highly pure adducts of alkylene oxides to compounds sufficiently reactive for the addition reaction, in particular to organic compounds having at least one active hydrogen atom, which process is advantageous as regards environmental conditions. The process should be reproducible under moderate reaction conditions and implementable with a maximum conversion number of the reactants, permit an exact control of the reaction conditions (pressure, temperature, flow rate, feed rate) and other critical parameters, largely suppress the occurrence of side reactions and result in adducts being largely free from monomeric alkylene oxides.

Moreover, an object of the invention was the making available of a device for carrying out the process of the invention.

The invention relates to a process for preparing a highly pure adduct of one or more alkylene oxide(s) to a compound being sufficiently reactive for the addition reaction, said process being carried out in a reaction system designed as a loop-type reactor including a reservoir and comprising the steps of (a) feeding a compound sufficiently reactive for the addition reaction to the reaction system and circulating said compound in the whole system;

(b) deaerating the whole reaction system and injecting an inert gas;

(c) adding, as a first step of a reaction cycle, said alkylene oxide(s) with mixing, said addition step taking place at a point of the reaction system which is upstream of a heat exchanger which is installed in the loop and serves as a means for heating;

(d) heating the partial amount of the reaction mixture containing freshly admixed alkylene oxide(s) during passage through said heat exchange to a temperature allowing a substantial degree of conversion of the reactants in the course of said passage;

(e) immediately cooling, after reaching said substantial degree of conversion of said reactants, said partial amount of the reaction mixture to a holding temperature allowing substantially no side reaction;

(f) holding said reaction mixture having reached said desired degree of conversion of said reactants in said loop-type reactor at a holding temperature allowing substantially no side reaction;

(g) freshly admixing said alkylene oxide(s) in accordance with step (c) for a new reaction cycle; and optionally (h) releasing the reaction product(s) from said reaction system as soon as the desired degree of alkoxylation is achieved.

The invention also relates to a loop-type reactor comprising a reservoir 1, at least one loop 2, 22 connected to the reservoir 1 by means of an outlet 11, 16 and an inlet 12, 17 comprising a means 3, 23 for circulating the liquid reaction mixture, at least one heat exchanger 4, 24, optionally one or more means 5, 25 for the turbulent feeding of the reaction mixture into the reservoir 1 or other means for generating turbulence of the reaction mixture in the reservoir 1, means 6, 26 for feeding gaseous or liquid alkylene oxides and means 7 for cooling the reaction mixture in the reservoir, characterized in that at least one of the heat exchangers 4, 24 is designed for heating a part of the reaction mixture and that means 8, 28 are provided by means of which the gas phase above the reaction mixture can be separately circulated.

Surprisingly, a large number of substances is available with the process of the invention for the addition of highly pure adducts of one or more alkylene oxide(s) to a compound sufficiently reactive for the addition reaction, which substances play a great part in chemical-industrial manufacturing and which so far could be produced in such a pure form, if at all, only under conditions, which were hardly justifiable economically. Examples are non-ionic tensides, in particular with a water solubility exactly adjustable by means of the degree of alkoxylation, emulsifiers for technical and cosmetic purposes, polyether glycols for the production of polyurethanes, etc. The products obtained with the present process are either available at the same reaction temperature as in the prior art in a substantially higher yield and product quality or can be obtained with the same quality requirements as in the prior art within the framework of a substantially more rapid reaction.

The process of the invention—like comparable processes of the prior art—can be carried out in any conceivable reactor. Such reactors may be stirred tank reactors, loop-type reactors, autoclaves with suited stirring means or also other reactors known to a person skilled in the art for reactions between gases and liquids or between two liquids. For the reasons mentioned in detail in the following, however, a reactor known by the designation of "loop-type reactor" is used for the process of the invention, if one wants to utilize all advantageous variants of the process for the solution of the set objects.

This reactor consists of a usually, but not necessarily cylindrical reservoir whose lower portion is connected to the upper portion of the reservoir by means of a loop guided past the exterior of the reactor, i.e. a conduit-like connection. The reaction system formed by the reservoir and the loop is customarily supplemented by a means for circulating the reservoir content, which is located at a suited point, mostly downstream of the lower connection point of reservoir and loop, customarily a high-speed liquid pump, and possibly a heat exchanger. The latter serves regularly for dissipating the reaction heat formed during the exothermal reactions and can possibly utilize the heat withdrawn from the reservoir for other processes or process steps.

In the process of the invention the whole reaction system is customarily deaerated in the first step, i.e. freed from air and possibly also other gases not desired for the later addition reaction. This is done with means known to a person skilled in the art for this purpose such as vacuum pumps or the like. The reaction system is then filled with an inert gas or a mixture of several inert gases. This process is customarily repeated in order to remove oxygen and other gases detrimental to the addition reaction from the system to a very high degree. Nitrogen, argon or carbon dioxide are e.g. used as inert gases. For reasons of its better availability and thus of its low price nitrogen is used with preference.

However, other inert gases can also be used inasmuch as they do not interfere with the later addition reaction.

The addition reaction to be carried out according to the invention takes place between a compound sufficiently reactive for such an addition reaction and an alkylene oxide or several alkylene oxides. In an embodiment preferred according to the invention compounds, as a rule organic compounds, which are sufficiently reactive for the addition reaction and which contain at least one reactive hydrogen atom, are used as a compound sufficiently reactive for the addition reaction. The same is bonded to an organic molecule residue via an oxygen atom, a nitrogen atom or a sulfur atom in the compounds coming into consideration.

Especially preferred examples of such compounds are alcohols, thiols, amines, carboxylic acids and their amides or also mixtures of compounds of said compound families, without limiting the invention to them. Special examples which are used in large quantities and advantageously, since products obtained from them by means of alkoxylation are broadly used in the industry, are fatty alcohols, especially preferred fatty alcohols having 8 to 18 carbon atoms, fatty amines, especially preferred also such with 8 to 18 carbon atoms, fatty acids, especially preferred such having 8 to 18 carbon atoms, and their derivatives. The latter include e.g. (fatty acid) amides, monoglycerides, sugar esters and others. Glycols or also short-chain monohydric or polyhydric alcohols having 2 to 6 carbon atoms are used with preference for the production of polyethers.

Compounds used according to the invention as co-reactants of the aforementioned compounds are alkylene oxides. A single alkylene oxide can be used according to the invention or several alkylene oxides can be used. If several alkylene oxides are used, it is a preferred embodiment of the invention to react two alkylene oxides concurrently with the aforementioned compounds. In a further preferred embodiment the two alkylene oxides used in this case have different reactivities with respect to the aforementioned compounds and/or the intermediate products which have been formed from the aforementioned compounds by means of the addition of one or several molecules of an alkylene oxide. The last-mentioned intermediate products are called for short primary adduct intermediate products in the following.

In a further, also preferred embodiment of the process of the invention it is also possible to react two alkylene oxides, which have regularly different reactivities with respect to the aforementioned organic compounds or the primary adduct intermediate products, successively with the aforementioned starting compounds or primary adduct intermediate products. In this fashion, defined block copolymers are available in a manner which can be carried out surprisingly simple and with a high yield as will be described in detail in the following.

As the alkylene oxides, ethylene oxide, propylene oxide, butylene oxide and/or their higher homologues and/or their isomers come into question with special preference. As already indicated above, mixtures of said alkylene oxides can also be used, which are added at different points of the reaction system, but react in parallel with the aforementioned starting compounds or the primary adduct intermediate products. In the same fashion, it is possible in a likewise preferred embodiment of the process of the invention to cause two alkylene oxides possibly also added successively at different points of the reaction system to react successively with the aforementioned starting compounds or the primary adduct intermediate products. Due to the importance of the products which can be produced with them, ethylene oxide and propylene oxide are especially preferred as the alkylene oxides. If two alkylene oxides are used, ethylene oxide is used as the more reactive alkylene oxide and propylene is used as the less reactive alkylene oxide in an embodiment which is especially preferred according to the invention.

In the process of the invention the reaction system is filled with the compound used as the starting compound and being sufficiently reactive for the addition reaction after the first step of deaerating and filling with inert gas. It must be observed that due to the subsequent addition reaction the volume of the reaction mass increases and that a corresponding increase in volume must be allowed for if specific properties are desired (in particular molecular weight and/or degree of alkoxylation). However, this forms part of expert ability and does not differ from the control of comparable reactions of the prior art.

The starting compounds from the group specified in greater detail above, which come into consideration, are customarily present as liquid substances under the reaction conditions to be used for the addition reaction with alkylene oxides so that the reaction can be carried out in substance, i.e. without the co-use of a solvent. In any case this must be considered as an especially preferred embodiment of the process of the invention, since a separation of a co-used solvent is omitted in this case. The making available of large amounts of suitably preconditioned solvents, e.g. their deaerating and/or gassing with a protective gas, is also omitted. Moreover, the installations used for carrying out the reaction may also have smaller dimensions, which has an advantageous effect on the economic efficiency of the process.

However, within the framework of specific problem definitions it is also possible to use one solvent or a mixture of several solvents. This may be advantageous if the viscosity of the reaction mixture increases in the case of aimed at higher degrees of alkoxylation and renders a satisfactory processing, cooling, etc. of the reaction mixture more difficult. In such a case one solvent or several solvents can be selected which do not render the reaction of the reactants more difficult under the reaction conditions or even compete with the reactants for the reaction. The selection of such solvents can be made by a person skilled in the art on the basis of his or her expert knowledge without inventive activity. Suited solvents are e.g. esters and ethers. In any case, protic solvents are not suited due to the possibility of their reaction with alkylene oxides.

To ensure an optimum contact of the reactants with each other, the reaction mixture is, according to the invention, circulated in the reaction system. This is done in a manner known per se to a person skilled in the art, e.g. by means of customary high-speed pumps which allow an exact adjustment of the flow rate of the liquid reaction mixture in the reaction system. Such pumps may e.g. be installed in the reaction system at a point between the reservoir and the heat exchanger(s), especially preferred between an outlet in the lower portion of the reservoir and the lower end of the heat exchanger (and/or the heat exchangers, if several are used).

After a specific flow rate of the reaction mixture in the reaction system, i.e. in the reservoir and the loop and/or loops, has been achieved and the reaction mixture has a specific temperature whose exact value is determined as a function of requirements which will be explained in greater detail in the following, an alkylene oxide is incorporated into the circulating reaction mixture (or several alkylene oxides are added at the same time or successively). This will be explained in greater detail in the following by means of the reaction with propylene oxide and/or by means of a reaction of the starting compounds and/or the primary adduct intermediate products with ethylene oxide and propylene oxide without the invention being limited to this; the aforementioned higher homologues of said alkylene oxides may just as well be used.

If one of the starting compounds mentioned above in detail is to be reacted with propylene oxide, it is, according to the invention, added to the reaction system at a point which is located behind the outlet of the reaction mixture from the reservoir in its lower area in the direction of flow and customarily also behind the pump installed for ensuring a specific flow rate of the reaction mixture, but before a heat exchanger installed in the loop and serving as a means for heating. In a preferred embodiment of the process the alkylene oxide, preferably the propylene oxide is admixed before the heat exchanger in a substantially homogeneously distributed manner. The advantage of this is that the reaction mixture supplied to the heat exchanger serving for heating contains the alkylene oxide component, preferably the propylene oxide, in uniformly distributed fashion, and it is thus ensured that the addition reaction can take place to the greatest possible extent as soon as the minimum temperature required for the start of the reaction has been achieved. In order to prevent side reactions of the propylene oxide, in particular rearrangement reactions to allyl alcohol, the reaction mixture is, prior to the incorporation of the propylene oxide, kept at a temperature at which substantially no side reactions take place, but a reaction with the component intended for the addition reaction does also not take place as yet. This is preferably carried out by cooling the reaction mixture in the reservoir by suited means explained in greater detail in the following.

The reaction mixture driven by the circulating means or the pump, which contains homogeneously distributed alkylene oxide, preferably propylene oxide, is now supplied to the heat exchanger serving for heating via the loop. It became surprisingly apparent that, if the heat exchanger is not used for cooling the reaction mixture heated to the reaction temperature at another point, but for its rapid heating to the reaction temperature, a largely complete addition of the alkylene oxide, preferably the propylene oxide, to the starting compound or to the primary adduct intermediate product can be achieved without the considerable occurrence of side reactions of the alkylene oxide such as rearrangements to non-reactive compounds.

During passage through the heat exchanger the reaction mixture containing freshly admixed alkylene oxide, e.g. propylene oxide, is heated to a temperature making an essential degree of conversion of the reactants possible. According to the invention it is understood by this that a temperature is reached during heating of the reaction mixture containing alkylene oxide on its flow through the heat exchanger, at which the admixed alkylene oxide is added to the compound sufficiently reactive for the addition reaction by at least 70% of the added amount, preferably at least 85% of the added amount and especially preferred at least 95% of the added amount. The adjustment of the temperature to a value permitting substantially a complete addition of the admixed alkylene oxide to the co-reactant until re-entry of the reaction mixture into the reactor vessel during the flow of the reaction mixture containing the alkylene oxide through the heat exchanger is especially preferred.

This value depends of course on several parameters, e.g. on the reactivity of the participating alkylene oxide or of the compound also participating as a reactant, on the type and amount of the catalyst, on the flow rate of the reaction mixture and on further parameters. If ethylene oxide is used as the alkylene oxide, a temperature of the reaction mixture of more than 100° C., preferably of 120° and 200° C., is especially preferred according to the invention. If propylene oxide is used as the alkylene oxide, the temperature of the reaction mixture is preferably above 120° C., preferably between 150° and 220° C., after passage through the heat exchanger. A still decisive parameter in the selection of the temperature is that, on the one hand, no or substantially no side reactions of the participating alkylene oxide(s) occur, but that, on the other hand, the reaction, based on the amount of the used alkylene oxide takes place as completely as possible and during a reaction time suitable for practice. A surprisingly high reaction rate can be achieved according to the invention and, despite this, a high product quality and a high degree of conversion can be achieved.

As soon as the desired substantial degree of conversion is achieved, i.e. at the earliest when the reaction mixture leaves the heat exchanger, but at the latest when it enters the reservoir again, the reaction mixture is immediately cooled according to the invention to a holding temperature allowing substantially no side reactions. This is the temperature at which the reaction mixture is held in the reservoir for a certain period of time, i.e. flows from the upper inlet area to the lower outlet area without being substantially subjected to a reaction, in particular without being subjected to side reactions of the participating reactants or the formed primary adduct intermediate products. The cooling of the reaction mixture is achieved in preferred embodiments by introducing the reaction mixture into the reaction mixture held in the reservoir, by spraying it into the gas space of the reservoir above the holding zone, by introducing it into the reaction mixture in the holding zone through a nozzle or by mixing it into the same in a turbulent fashion. The reaction mixture held in the reservoir is kept at a low temperature by means of suitable cooling means in especially preferred embodiments. These cooling means are especially preferred in or at the reservoir wall, such as a coolant flowing or circulating in the reservoir shell, in particular a cooling fluid such as a cooling liquid or a cooling gas. Alternatively, cooling can also be brought about by means of a second loop in which a heat exchanger with a cooling effect and known per se is installed.

For the step of the cooling of the reaction mixture being at the reaction temperature (or due to the exothermal nature of the reaction even above it) to the holding temperature it is decisive that the step is carried out so rapidly that the occurrence of undesired side reactions is substantially avoided. This can be surprisingly achieved in the loop-type reactor described in the following. The reaction mixture flows at a given temperature with special preference at such a rate through the reaction loop that the addition reaction of the alkylene oxide, e.g. of the propylene oxide, to the compound sufficiently reactive for the addition reaction, i.e. the organic compound with a reactive hydrogen atom which is used as the starting substance, is largely completed upon re-entry of the reaction mixture into the reservoir, based on the added amount of alkylene oxide in the corresponding volume fraction of the reaction mixture.

In a preferred embodiment in the process of the invention the temperature in the gas space of the reservoir above the holding zone is kept at least 5° C. below the temperature prevailing in the reservoir in which the largest partial amount of the reaction mixture is held without the occurrence of side reactions to a substantial extent. This is of special advantage because the reaction mixture flows through the cool gas phase already prior to entering the liquid phase held in the reactor vessel and kept at low temperature ("holding temperature") or—if a jet pipe is used—even entrains it and is cooled thereby relatively rapidly.

The liquid reaction mixture which only contains alkylene oxide(s) to a small extent, but mainly the starting compound and the primary adduct intermediate product and optionally the solvent, and thus has reached the desired substantial degree of conversion, is kept at a temperature ("holding temperature") substantially allowing no side reactions. This is—depending on the alkylene oxide used—with special preference 80° to 120° C. The temperature is e.g. adjusted to a value ranging from 80° to 100° C., if only ethylene oxide is used, and to a value ranging from 80° to 120° C. if only propylene oxide is used. An addition of alkylene oxide to the starting compound or to the primary adduct intermediate product formed in the preceding reaction step does not take place or only takes place to a small extent as compared with the actual reaction at this temperature. As opposed to the prior art, the reaction mixture in the reservoir is kept at a temperature being below the minimum temperature at which an addition of the alkylene oxide(s) to the starting compound or the primary adduct intermediate product takes place to a significant extent or to an extent being substantial for practical considerations. The advantage of this is that the reacting partners remain at or even above the minimum reaction temperature only for a short period of time which is just sufficient for the addition of the reactive alkylene oxide to the starting compound or the primary adduct intermediate product. Due to the immediate cooling it is prevented that undesired side reactions of the reactants or the (intermediate) products take place, which reduce the yield or impair the quality of the final products, e.g. due to a too broad distribution of homologues.

After the reaction mixture has flowed through the reservoir at the aforementioned low holding temperature—regularly from the top to the bottom—, it leaves the reservoir again, namely in the presently described case through the outlet located in the lower portion of the reservoir and enters the loop for a renewed addition reaction with admixing of the alkylene oxide, heating of the mixture in the heat exchanger, etc. according to the process described in detail above.

In the presently described case of the sole conversion of the compound sufficiently reactive for the addition reaction with an alkylene oxide, e.g. with propylene oxide, an adduct of the desired degree of alkoxylation or degree of propoxylation, respectively, is produced after a repeated passage of the reaction cycle. It has a high product quality, i.e. a narrow distribution of homologues. Such a product can be produced under economically interesting conditions and is obtained in high purity, i.e. with an only extremely low content of monomeric alkylene oxide. Moreover, the operation sequence allows a considerable conversion of the alkylene oxide without the process air containing significant amounts of alkylene oxide. The achievable conversion number is by far higher than in the prior art and the implementation of the process according to the invention permits an exact control of the reaction obtaining products with the desired properties.

In the following the reaction of a compound sufficiently reactive for the addition reaction with two alkylene oxides will be described taking the reaction with ethylene oxide and propylene oxide as an example. This type of reaction corresponds to a preferred embodiment of the process of the invention, because "tailored" adducts with defined properties can be synthetized thereby, in particular mixed adducts with randomly distributed ethoxy and propoxy groups or block adducts with blocks from several ethoxy or propoxy groups. A loop-type reactor is used for this reaction which largely corresponds to that used for the reaction with a single alkylene oxide according to the aforementioned description. As opposed to this, the loop-type reactor used with preference for the addition of two differently reactive alkylene oxides has, however, two separate loops which may also have one heat exchanger each in an especially preferred embodiment. It corresponds to an operation sequence according to the invention, which is used with advantage, if the one heat exchanger serves for heating the flow of the reaction mixture, to which less reactive alkylene oxide is admixed, whereas the other heat exchanger serves for dissipating the reaction heat formed during the addition of the more reactive alkylene oxide and for dissipating the heat supplied by heating and possibly of the reaction heat supplied or formed during the addition of the less reactive alkylene oxide.

In the embodiment of the process of the invention, in which two alkylene oxides of different reactivity, with special preference ethylene oxide and propylene oxide, are added to the compound sufficiently reactive for the addition reaction according to the group of compounds specified above, the entire reaction system is also deaerated and filled with inert gas in a first step. As in the case of the reaction with an alkylene oxide an individual inert gas or a mixture of several inert gases can be used. Nitrogen alone is used with special preference for the reasons indicated above.

The compound sufficiently reactive for the addition reaction which is included in the group of the compounds specified in greater detail above, is then fed into the reaction system and circulated by means for circulating in the loops branching off from the reservoir and guiding into the same and in the reservoir itself. One of the two heat exchangers is used as heat exchanger serving for heating; the less reactive alkylene oxide, with preference propylene oxide, is fed into the loop comprising this heat exchanger. The other one of the two heat exchangers serves for cooling the reaction mixture; the more reactive alkylene oxide, with preference ethylene oxide, is fed into the loop comprising this heat exchanger. The heat exchanger does not only dissipate the reaction heat released during the addition of ethylene oxide, but also the heat supplied due to the heating of the portion of the reaction mixture flowing in the other loop to the reaction temperature necessary for the addition of propylene oxide and the reaction heat released during the addition of the propylene oxide.

In a preferred embodiment of this process the more reactive alkylene oxide is added to the reaction mixture flowing through the reaction system including both loops at a point downstream of the cooling heat exchanger, but upstream before the re-entry of the reaction mixture into the reservoir. Alternatively, the more reactive alkylene oxide can be directly fed into the top space of the reservoir by means of a distributing means, e.g. by means of a nozzle. In the exemplified case of the use of ethylene oxide as the more reactive alkylene oxide, it is fed into the loop downstream of the heat exchanger acting coolingly or directly into the head space of the reservoir. At this point, the reaction mixture is at a temperature which is possibly only slightly above the value which must be kept as a minimum value for the rapid reaction of the ethylene oxide with the organic compound, which is suitable for practical purposes. At this temperature the ethylene oxide reacts violently with the starting compound (or, in a later reaction cycle, with the primary adduct intermediate product) releasing heat which is released to the reaction mixture held in the reservoir or dissipated through the cooling means integrated in the reaction system. Upon re-entry of the reaction mixture into the reservoir, the reaction mixture has reached a substantial degree of conversion which, based on the added ethylene oxide, is at least 70% of the added amount, preferably at least 85% of the added amount, with very special preference at least 95% of the added amount. An operation sequence in which the reactants, i.e. the ethylene oxide and the organic compound, have reacted substantially completely in the sense of an addition reaction is especially preferred, because it is advantageous in view of economic efficiency.

The less reactive alkylene oxide, in the present example the propylene oxide, preferably reacts with the starting substance or with the primary adduct intermediate product in the other loop. In the present case the latter can be either an intermediate product containing propoxy residues from an earlier cycle of the addition of propylene oxide or an intermediate product containing ethoxy residues from the cycle of the addition of ethylene oxide to the organic starting compound or also an intermediate product which contains both ethoxy residues and propoxy residues from earlier reaction cycles. The reaction with propylene oxide occurs substantially in the same manner as this was already described above for the addition reaction with propylene oxide alone. The propylene oxide as the less reactive alkylene oxide is thus added to the reaction mixture flowing through the reaction system including both loops at a point located upstream before the heating heat exchanger, but downstream after the reaction mixture has flowed out of the reservoir.

The reaction mixture driven by the circulating means, which is relatively cool at this point and at any rate cooler than would be required for the addition reaction of propylene oxide, then flows into the heat exchanger intended for heating the reaction mixture and is heated to a temperature above the minimum temperature required for the addition reaction of propylene oxide. The temperature and the reaction rate are selected in coordination with each other so that the reaction of the propylene oxide with the organic compound upon re-entry of the reaction mixture into the reservoir has reached a substantially degree of conversion. Preferably the degree of conversion is, based on the added propylene oxide, at least 70% of the added amount, preferably at least 85% of the added amount, especially preferred at least 95% of the added amount of propylene oxide. It is especially preferred according to the invention that the addition of the admixed propylene oxide to the organic compound or the primary adduct intermediate products has substantially completely occurred in the reaction mixture upon the re-entry of the reaction mixture into the reservoir.

Upon re-entry of the reaction mixture which has reached the desired substantial degree of conversion into the reservoir, the mixture is immediately cooled to a temperature allowing substantially no side reactions, at which it is held in the reservoir or flows through it, with preference from the top to the bottom. The temperature is with special preference in the range of from 80° to 120° C. The advantage of this is that side reactions both of the reactants, in particular of the alkylene oxides, but also of the primary adduct intermediate products can be largely suppressed and consequently the final products are obtained in a high yield, based on the amounts of the used reactants, and in a high purity and thus in a high quality.

In the case of the joint use of several alkylene oxides the holding temperature is adjusted to a value in an especially preferred embodiment of the process of the invention, which is above the minimum reaction temperature of the more reactive alkylene oxide, but below the minimum reaction temperature of the less reactive alkylene oxide. The temperature of the reaction mixture is advantageously at a temperature being by 1° to 5° C. above the temperature at which the more reactive alkylene oxide just reacts at a reaction rate suitable for practical purposes with the compound sufficiently reactive for the addition reaction. This is especially preferred because the reaction mixture flowing in the one loop of the reaction system comprising a heat exchanger with cooling function can be reacted with the more reactive alkylene oxide, in the present case, ethylene oxide, without having to fear side reactions. However, the temperature is too low for a reaction with the less reactive alkylene oxide, in the present case propylene oxide; it can only be added to the organic compound or the primary adduct intermediate products after a local heating of the reaction mixture by means of the heat exchanger serving for heating.

In a further preferred embodiment of the process according to the invention the reaction mixture guided in the loop or the loops, respectively, is re-fed to the reservoir via one jet pipe (each). Such a jet pipe is known from the prior art. There and in the present invention it serves for re-combining the reaction mixture circulating in the loop(s) with the reaction mixture held in the reservoir. This is done with entraining part of the gas phase above the reaction mixture held in the reservoir and produces a strong turbulence during addition by mixing. This is of considerable advantage since it brings about a considerable homogenizing of the mixture and a rapid cooling of the reaction mixture reacted with the alkylene oxides, ensures a narrow distribution of homologues and thus ensures a high uniformity and quality of the product.

It corresponds to a further preferred embodiment of the process of the invention to circulate the gas phase present above the reaction mixture in the reservoir in a separate gas loop. It is usually guided in such fashion that it also flows into the jet pipe. An essential advantage of this separate gas flow control consists in that the separate gas loop offers the possibility of feeding an alkylene oxide into the reaction system. The same can react with the compound sufficiently reactive for the addition reaction in the case of a suitable temperature control and flow rate, it being possible to select the reaction conditions in such fashion that the distance prior to the entry of the reaction mixture into the reservoir is sufficient for achieving a substantially complete degree of conversion as it is desired prior to re-entry of the reaction mixture into the reservoir. These conditions are e.g. given if the alkylene oxide used for this preferred embodiment is ethylene oxide and the separate gas flow control provides for a feeding of the gas into the top portion of a jet pipe via which the cooled reaction mixture is again supplied to the reservoir in turbulent fashion entraining the gas phase. Upon entry of the reaction mixture into the reservoir substantially the whole amount of ethylene oxide has been added to the organic compound, and the reaction mixture is immediately cooled to a temperature which allows substantially no occurrence of side reactions.

A further advantage of this operation sequence is that upon the reaching of the desired degrees of alkoxylation the reaction can be achieved rapidly and without releasing to the environment residual, unreacted alkylene oxide by simply terminating the feeding of alkylene oxide and allowing the alkylene oxide remaining in the gas space to complete the reaction so that also the last residual amounts of the reactive alkylene oxides are utilized for the addition reaction; in the waste gas, a content of alkylene oxides is forbidden. At the same time, a cooling of the reaction mixture to a temperature is effected by a further circulating of the reaction mixture without the release of reaction heat or without a further heating of the reaction mixture in the loop with the less reactive alkylene oxide (e.g. propylene oxide), at which the side reactions both of the alkylene oxides and the alkoxylation products do not take place any longer. Thus, a high-quality product free from monomers with a narrow distribution of homologues is obtained in an economic and ecologically acceptable fashion.

The invention is now further explained with reference to the Figures.

FIG. 1 shows a loop-type reactor according to the invention with a loop which comprises in the shown embodiment a heat exchanger for the heating of the reaction mixture, e.g. for the reaction of a compound sufficiently reactive for the addition reaction with propylene oxide. However, it is also conceivable that this heat exchanger can be used to cool if the addition of a reactive alkylene oxide, e.g. of ethylene oxide, requires the cooling of the reaction mixture to avoid side reactions.

Figure 2:
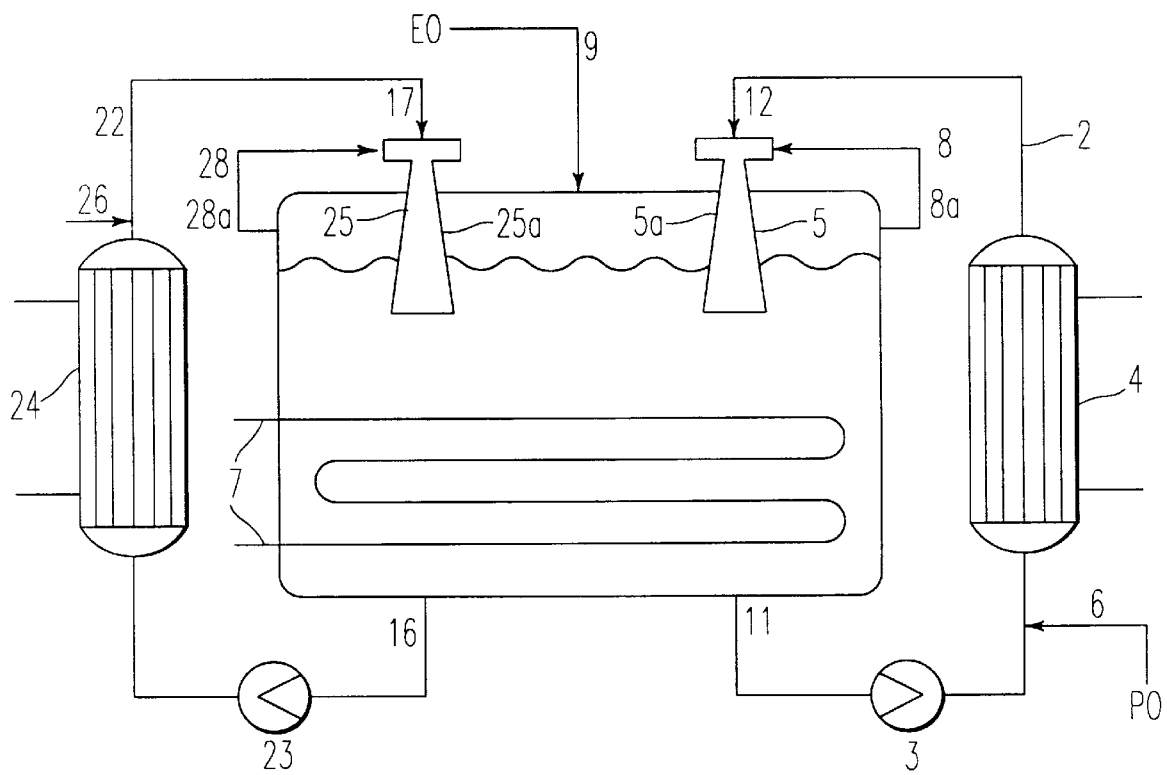

FIG. 2 shows a loop-type reactor according to a further preferred embodiment for the operation sequence with feeding of two differently reactive alkylene oxides, e.g. ethylene oxide and propylene oxide.

The invention also relates to a loop-type reactor comprising a reservoir 1, at least one loop 2, 22 connected to the reservoir 1 by means of an outlet 11, 16 and an inlet 12, 17 comprising a means 3, 23 for circulating the liquid reaction mixture, at least one heat exchanger 4, 24, optionally one or more means 5, 25 for the turbulent feeding of the reaction mixture into the reservoir 1 or other means for generating turbulence of the reaction mixture in the reservoir 1, means 6, 26 for feeding gaseous or liquid alkylene oxide(s) and means 7 for cooling the reaction mixture in the reservoir, wherein at least one of the heat exchangers 4, 24 is designed for heating part of the reaction mixture and that means 8, 28 are provided by means of which the gas phase above the reaction mixture can be separately circulated.

The loop-type reactor according to the invention was already described in connection with the process of the invention as regards its function. In a preferred embodiment of the reactor the means 8, 28 for the separate circulating of the gas phase is/are one or several gas loops 8a, 28a separated from the circulation of the liquid reaction mixture. They are designed according to this embodiment in such fashion that the gas phase above the reaction mixture held in the reservoir 1 can be withdrawn at one or several point(s) located at a suited distance above the liquid level in the upper portion of the reservoir 1. The gas phase is substantially inert gas. However, (if ethylene oxide is used, which is gaseous under the reaction conditions) certain residual amounts of unreacted ethylene oxide and propylene oxide may be present in the gas phase. Moreover, it is possible that the ethylene oxide is added to the reaction system via the gas phase. In this case the gas phase consists largely of inert gas and ethylene oxide.

In a preferred embodiment of the reactor of the invention a means 9 for feeding a gas, e.g. the more reactive alkylene oxide such as ethylene oxide, is located in the upper portion of the reservoir 1, i.e. in the area of the gas space. This means may be a distributing system such as a nozzle via which the gas, e.g. ethylene oxide, is directly introduced into the gas space of the reservoir and is thus available for the rapid reaction with the turbulently flowing reaction mixture. This means can be used instead of the means for gas supply via the reactor loop of the reservoir of the invention or together with it.

Various means for the turbulent feeding of the reaction mixture into the reservoir, which are known per se to a person skilled in the art, can be used in the reactor according to the invention. Such means may e.g. be nozzles with a small cross-section, which generate a turbulence, distributor plates or blades or further means known to a person skilled in the art. According to an especially preferred embodiment of the reactor the means 5, 25 for the turbulent feeding of the reaction mixture into the reservoir 1 is/are one or several jet pipe(s) 5a, 25a. Such jet pipes generate a strong turbulence due to their special construction, in particular due to the conical outlet, with forced increase in the flow rate and make it possible due to this that the reaction mixture is mixed homogeneously and products with a relatively narrow distribution of homologues are obtained. Moreover, such jet pipes aid in the dissipation of the reaction heat or the heat supplied for the addition of the less reactive alkylene oxides. Thus, they contribute to rapidly reducing the temperature of the reaction mixture to a value, at which side reactions do not take place any longer.

The embodiment of the loop-type reactor according to the invention is especially preferred according to which the gas flow control is such that the separately circulated gas phase is re-introduced into the reservoir 1 via the jet pipe(s) 5a, 25a. This is advantageous because, due to this, the possibility is given to add the alkylene oxide in gaseous form, here ethylene oxide, to the gas circulation in a fashion which permits an immediate complete reaction prior to the re-entry of the reaction mixture into the reservoir or the cooled reaction mixture held therein. Due to this, side reactions of the alkylene oxide, on the one hand, and of the (intermediate) products, on the other hand, are reliably prevented. On the other hand, no enrichment of alkylene oxide in the reaction mixture takes place, which always entails the risk of a sudden "self-acceleration" of the reaction. Hence, the immediate addition of the alkylene oxide to the organic starting compound or the primary adduct intermediate products is also advantageous in the interest of safety.

The invention is further explained in the following examples without being restricted to them.

Comparative Example 1

Production of a propoxylated glycerine (theoretical molecular weight: 3,900 g/mole)

2,500 g of a propoxylated glycerine (molecular weight: 1,000 g/mole) together with 1% potassium hydroxide as catalyst (calculated as 100% KOH) were weighed into a conventional stirred tank with an effective volume of about 15 l, which was equipped with a stirrer and heating/cooling surfaces, and mixed. The reaction mixture was heated to 120° C., dried for 0,5 h under vacuum and then rendered inert by flushing it two times with nitrogen.

Subsequently, a total of 6,250 g of propylene oxide was incorporated at a maximum reaction temperature of 135° C. over a period of time of about 3.5 h in such fashion that the pressure in the reactor did not exceed 5 bar. After termination of the supply of propylene oxide, the completion of the reaction was allowed to take place at 140° C. for 15 minutes. Finally, the product was freed from volatile compounds at 120° C. under a vacuum for further 30 minutes.

The reaction product had a hydroxyl number of 51, which corresponds to a molecular weight of 3,400 g/mole (theoretical molecular weight according to stoichiometry: 3,900 g/mole).

EXAMPLE 1

Production of a propoxylated glycerine (theoretical molecular weight: 3,900 g/mole)

2,500 g of a propoxylated glycerine with a molecular weight of 1,000 g/mole (corresponding to a hydroxyl number of 169) was weighed in together with 1% potassium hydroxide (calculated as 100% KOH), fed into a reactor 1 according to FIG. 1 with an effective volume of about 10 l and thoroughly circulated. The reaction mixture was heated to 120° C. by means of the heat exchanger 4, dried by applying a vacuum for a period of time of 0,5 h and rendered inert by flushing it twice with nitrogen.

Thereafter, 6,250 g of propylene oxide were incorporated in an amount of 3,000 g/h via a mixer at 6 (FIG. 1) and with a circulating performance of 50 l/h. The temperature of the heat exchanger 4 was adjusted to 160° C. By controlling the circulating performance and the amount of incorporated propylene oxide the pressure in the reactor was kept at a maximum of 4 bar. The temperature in the reservoir 1 was kept at 120° C. by means of the cooling means 7 during the reaction.

After the termination of the supply of propylene oxide, the reaction mixture was circulated for further 15 minutes. Thereafter the product was freed from volatile components at 120° C.

The product prepared in this fashion according to the invention, which had a theoretical molecular weight resulting from stoichiometry of 3,900 g/mole had a hydroxyl number of 47, which corresponds to a molecular weight of 3,650 g/mole. Thus, a product of a better quality was achieved in the case of the same performance as in the comparative example 1.

EXAMPLE 2

Production of a propoxylated glycerine (theoretical molecular weight: 3,900 g/mole)

It was proceeded as in example 1, and substantially the same amounts of reactants were used. The amount of the incorporated propylene oxide per time unit was, however, increased to 6,000 l/h. The holding temperature in the reservoir 1 was 130° C., and the reaction temperature in the heat exchanger 4 was 160° C. Apart from this, the same reaction conditions as in example 1 prevailed.

A product with a hydroxyl number of 48 which corresponds to a molecular weight of 3,550 g/mole (theoretical MW: 3,900 g/mole) was obtained. As compared with the comparative example 1, a product of the same quality was obtained, but with an increased throughput.

Comparative example 2

Production of a propoxylated butyl diethylene glycol 2,000 l of butyl diethylene glycol were mixed with 120 g potassium methylate as the catalyst as in the comparative example 1 in a customary stirring tank, dried at 100° C. under vacuum and then rendered inert.

Then 8,000 g of a propylene oxide containing 2% of ethylene oxide was incorporated in an amount of 1,600 g/h at a reaction temperature of 125° C. in such fashion in a first step that the pressure in the reactor did not exceed 3 bar. After the termination of the incorporation, the completion of the reaction was allowed to take place for 0,5 h. The reactor was then emptied with the exception of 3,000 g of the reaction product of the first step.

In a second reaction step 6,000 g of the alkylene oxide mixture was added to the intermediate product, the other reaction conditions being the same. After the addition of the entire amount of alkylene oxide, the completion of the reaction of the reaction mixture was allowed to take place at 130° C. for further 2 h. The reaction mixture was subsequently freed from volatile components under a vacuum of 15 mbar for a period of time of 20 minutes.

The thus obtained reaction product had a hydroxyl number of 40 and a iodine number of 9.

EXAMPLE 3

Production of a propoxylated butyl diethylene glycol 8,000 g of the alkylene oxide mixture according to the comparative example 2 were added to 2,000 g of butyl diethylene glycol and 120 g of potassium methylate in a reactor according to FIG. 1 in a first reaction step and caused to react under conditions corresponding to those of example 1 with the exception that the holding temperature in the reservoir 1 was 115° C. and the temperature in the heat exchanger 4 was adjusted to 135° C.

After this reaction step, the reaction was interrupted and the reactor was emptied with the exception of 3,000 g of the intermediate product. 6,000 g of the alkylene oxide mixture according to the comparative example 2 were added again in a second reaction step, the other conditions being as indicated above. After the termination of the addition, the completion of the reaction was allowed to take place for about 20 minutes, and volatile substances were subsequently removed at 100° C. under a vacuum.

The obtained reaction product had a hydroxyl number of 32 and a iodine number of 5. The theoretical hydroxyl number calculated from the stoichiometry of the batch was 24.

I claim:

1. A process for preparing a highly pure adduct of one or more alkylene oxide(s) to a compound which is sufficiently reactive for an addition reaction, said process being carried out in a reaction system designed as a loop-type reactor having a reservoir and comprising the steps of:

(a) feeding a compound sufficiently reactive for the addition reaction to the reaction system and circulating said compound in a whole system;

(b) deaerating the whole reaction system and injecting an inert gas;

(c) adding, as a first step of a reaction cycle, said alkylene oxide(s) with mixing, said addition step taking place at a point of the reaction system which is upstream a heat exchanger which is assembled in the loop and serves as a means for heating;

(d) heating a partial amount of the reaction mixture containing freshly admixed alkylene oxide(s) during passage through said heat exchanger to a temperature allowing a substantial degree of conversion of the reactants in the course of said passage;

(e) immediately cooling, after reaching said substantial degree of conversion of said reactants, said partial amount of said reaction mixture to a holding temperature allowing substantially no side reaction;

(f) holding said reaction mixture having reached said desired degree of conversion of said reactants, in said loop-type reactor at said holding temperature allowing substantially no side reaction;

(g) freshly admixing said alkylene oxide(s) in accordance with step (c) for another reaction cycle; and optionally (h) releasing the reaction product(s) from said reaction system as soon as the desired degree of alkoxylation is achieved.

2. The process as claimed in claim 1 wherein nitrogen, argon or carbon dioxide are used as the inert gas.

3. The process as claimed in claim 1 wherein organic compounds containing at least one reactive hydrogen atom which is bound to the organic molecule residue via an oxygen atom, a nitrogen atom or a sulfur atom, are used as the compound sufficiently reactive for the addition reaction.

4. The process as claimed in claim 3 wherein alcohols, thiols, amines, carboxylic acids and/or their amides are used as the compound sufficiently reactive for the addition reaction.

5. The process as claimed in claim 1 wherein ethylene oxide, propylene oxide, butylene oxide or their isomers or their higher homologues or mixtures of said alkylene oxides or amounts of more than one of the above alkylene oxides, as single compounds fed consecutively or parallel in time, are used as said alkylene oxides, whereby ethylene oxide and/or propylene oxide are preferred.

6. The process as claimed in claim 1 wherein said alkylene oxide(s) is/are admixed to the reaction mixture in a substantially homogeneous manner.

7. The process as claimed in claim 1 wherein said reaction temperature is increased, depending on the alkylene oxide(s) used, to a value allowing a substantially complete addition of said admixed alkylene oxide(s) onto the reaction partner until to the reentry of said reaction mixture into said reservoir.

8. The process as claimed in claim 7 wherein said reaction temperature is above 100° C., if ethylene oxide is used.

9. The process as claimed in claim 7 wherein said reaction temperature is above 120° C., if propylene oxide is used.

10. The process as claimed in claim 1 wherein, at a given reaction temperature, the flow rate of said reaction mixture is selected such that the reaction is substantially completed at the time of reentry of said reaction mixture into the reservoir, based on the amount of alkylene oxide(s) added per unit volume of the reaction mixture.

11. The process as claimed in claim 1 wherein the temperature in the gas space of the reservoir above the holding zone is at least 5° C. below said holding temperature at which substantially no side reactions occur.

12. The process as claimed in claim 1 wherein said cooling of the reaction mixture is effected by turbulent admixture of said mixture into an (intermediate) product mixture held in the reservoir and maintained at a low holding temperature and/or by spraying said mixture into the gas space of said reservoir above the holding zone.

13. The process as claimed in claim 1 wherein said cooling of the reaction mixture held in said reservoir is effected by cooling means at or in the reservoir walls, respectively.

14. The process as claimed in claim 13 wherein said cooling means are selected from the group consisting of cooling agents circulated in the reservoir jacket, heat exchanger in a second loop and gas cooler being located outside said reservoir and adapted for cooling the gas phase.

15. The process as claimed in claim 1 wherein two alkylene oxides are reacted with said compound sufficiently reactive for the addition reaction, whereby mixed adducts and/or block adducts are formed.

16. The process as claimed in claim 15 wherein a reaction system comprising one heat exchanger serving for heating and another heat exchanger serving for cooling, each of them being installed in different loops connected to the reservoir, are employed for said reaction with two alkylene oxides.

17. The process as claimed in claim 16 wherein the more reactive alkylene oxide is fed to the reaction mixture flowing through the reaction system including said two loops at a point downstream the cooling heat exchanger but upstream a point of reentry of said reaction mixture into the reservoir, or is fed to the gas phase in the reservoir above the reaction mixture.

18. The process as claimed in claim 17 wherein the less reactive alkylene oxide is fed to the reaction mixture flowing through the reaction system including said two loops at a point upstream the heating heat exchanger but downstream a point of exit of the reaction mixture out of the reservoir.

19. The process as claimed in 18 wherein the reaction mixture is reentered into the reservoir after flowing through said loops via respective jet pipes.

20. The process as claimed in claim 11 wherein the gas phase present in the reservoir above the reaction mixture is circulated in a separate gas loop which optionally runs into said jet pipe.

21. The process as claimed in claim 17 wherein the more reactive alkylene oxide is fed into said separate gas loop and optionally is admixed to said reaction mixture being present in said reservoir by means of a jet pipe if two alkylene oxides are included in the reaction.

22. The process as claimed in claim 17 wherein the more reactive alkylene oxide is fed into said separate gas loop or into said reaction mixture fed into said reservoir by means of said jet pipe at a temperature which exceeds the temperature by 1° to 5° C., at which the more reactive alkylene oxide is still reacting with said compound sufficiently reactive for said addition reaction at a reaction rate suitable for practical purposes, if two alkylene oxides are included in the reaction.

23. The process as claimed in any of the claim 17 wherein said more reactive alkylene oxide is ethylene oxide and the less reactive alkylene oxide is propylene oxide.

24. The process as claimed in claim 1, wherein said holding temperature is 80° to 120° C.

25. The process as claimed in claim 2, wherein said inert gas is nitrogen.

26. The process as claimed in claim 8, wherein said reaction temperature is between 120° to 200° C.

27. The process as claimed in claim 9, wherein said reaction temperature is between 150° to 220° C.

28. The process as claimed in claim 18, wherein said less reactive alkylene oxide is propylene oxide.

* * * * *

UNITED STATES PATENT AND TRADEMARK OFFICE
CERTIFICATE OF CORRECTION

PATENT NO. : 5,811,595
DATED : Sept. 22, 1998
INVENTOR(S) : Vincent Simon Ellis

It is certified that error appears in the above-identified patent and that said Letters Patent is hereby corrected as shown below:

On title page, insert the following:

Foreign Application Priority Data

--[30] Jul. 8, 1994 [DE] Germany..............................44 24 130.5--

Signed and Sealed this

Sixteenth Day of February, 1999

Attest:

Attesting Officer

*Acting Commissioner of Patents and Trademarks*